US008541182B2

(12) United States Patent
Fishman et al.

(10) Patent No.: US 8,541,182 B2
(45) Date of Patent: Sep. 24, 2013

(54) BIOLOGICAL MARKER FOR INFLAMMATION

(75) Inventors: Pnina Fishman, Herzliya (IL); Sara Bar-Yehuda, Rishon le Zion (IL); Lea Madi, Rishon le Zion (IL)

(73) Assignee: Can-Fite Biopharma Ltd., Petach Tikva (IL)

( * ) Notice: Subject to any disclaimer, the term of this patent is extended or adjusted under 35 U.S.C. 154(b) by 310 days.

(21) Appl. No.: 12/819,945

(22) Filed: Jun. 21, 2010

(65) Prior Publication Data

US 2010/0256084 A1    Oct. 7, 2010

Related U.S. Application Data

(63) Continuation of application No. 10/565,238, filed as application No. PCT/IL2005/001279 on Nov. 30, 2005, now abandoned.

(60) Provisional application No. 60/632,198, filed on Dec. 2, 2004, provisional application No. 60/657,718, filed on Mar. 3, 2005.

(51) Int. Cl.
*G01N 33/53* (2006.01)
(52) U.S. Cl.
USPC ............................. 435/7.2; 435/4; 435/7.24
(58) Field of Classification Search
None
See application file for complete search history.

(56) References Cited

U.S. PATENT DOCUMENTS

| | | | |
|---|---|---|---|
| 2002/0119924 | A1 | 8/2002 | Bendele et al. |
| 2004/0016709 | A1 | 1/2004 | Felcman et al. |
| 2004/0137477 | A1 | 7/2004 | Fishman et al. |
| 2004/0167094 | A1 | 8/2004 | Fishman et al. |
| 2004/0229246 | A1 | 11/2004 | Fishman et al. |
| 2005/0065192 | A1 | 3/2005 | Yednock et al. |
| 2005/0074451 | A1 | 4/2005 | Yednock et al. |

FOREIGN PATENT DOCUMENTS

| | | |
|---|---|---|
| AU | 200051825 A1 | 10/2000 |
| JP | 2004-135657 A | 5/2004 |
| WO | 8505031 A1 | 11/1985 |
| WO | 2004036215 A2 | 4/2004 |
| WO | 2004038419 A1 | 5/2004 |
| WO | WO 2004/086034 A | 10/2004 |
| WO | WO 2005/063246 A1 | 7/2005 |

OTHER PUBLICATIONS

Aletaha et al., "The reumatoid arthritis patient in the clinic: comparing more than 1300 consecutive DMARD Courses" Rheumatology. vol. 41, pp. 1367-1374 (2002).
Baharav et al., "Antiinflammatory Effect of A3 Adenosine Receptor Agonists in Murine Autoimmune Arthritis Models" Journal of Rheumatology, vol. 32; No. 3, pp. 469-476 (2005).
Chan el al.. Molecular Action of Methotrexate in Inflammatory Diseases; Arthritis Research. vol. 4. No. 4: 4. pp. 266-273 (2002).
D. Krause, "Long-term combination therapy of rheumatoid arthritis: Methotrexate and parenteral gold" Zeltschrift fuer Rheumatol, vol. 57:No. 1, pp. 37-40, (see tables 1-7) (1998).
Schwartz et al. "Prediction of respiratory symptoms by peripheral blood neutrophils and eosinophils in the First National Nutrition Examination Survey (NHAHES I)" Chest 104; 1210-1215 (1993).
Lewis et al. "The Relation Between Peripheral Blood Leukocyte Counts and Respiratory Symptoms, Atopy, Lung Function, and Airway Responsiveness in Adults" Chest 119; 105-114 (2001).
B. A. Walker et al., "Adenosine A3 receptor expression and function in eosinophils", *American Journal of Respiratory Cell and Molecular Biology*, vol. 16, No. 5, pp. 531-537, May 1997.
P. G. Baraldi et al., "A3 Adenosine Receptor Ligands: History and Perspectives", *Medicinal Research Reviews*, vol. 20, No. 2, pp. 103-128, Mar. 2000.
Y. Kohno et al., "Activation of A3 Adenosine Receptors on Human Eosinophils Elevates Intracellular Calcium", *Blood*, vol. 88, No. 9, pp. 3569-3574, Nov. 1, 1996.
P. Fishman et al., "Evidence for involvement of Wnt signaling pathway in IB-MECA mediated suppression of melanoma cells", *Oncogene*, vol. 21, pp. 4060-4064, 2002.
P. Fishman et al., "Targeting the A3 adenosine receptor for cancer therapy: inhibition of Prostate carcinoma cell growth by $A_3AR$ agonist", *Anticancer Res.*, vol. 23, pp. 2077-2083, 2003.
L. Madi et al., "A3 adenosine receptor activation in melanoma cells: association between receptor fate and tumor growth inhibition", *J. Bio. Chem.*, vol. 278, pp. 42121-42130, 2003.
G. Ohana et al., "Inhibition of primary colon carcinoma growth and liver metastasis by the A3 adenosine receptor agonist IB-CF101", *British J. Cancer*, vol. 89, pp. 1552-1558, 2003.
P. Fishman et al., "An agonist to the A3 adenosine receptor inhibits colon carcinoma growth in mice via modulation of GSK-3β and NF-κB", *Oncogene*, vol. 23, pp. 2465-2471, 2004.
C. Szabo et al., "Suppression of macrophage inflammatory protein (MIP)-1α production and collagen-induced arthritis by adenosine receptor agonists", *British J. Pharmacology*, vol. 125, pp. 379-387, 1998.
J. Mabley et al., "The adenosine $A_3$ receptor agonist, $N^6$-(3-iodobenzyl)-adenosine -5'-N-methyluronamide, is protective in two murine models of colitis", *European J. Pharmacology*, vol. 466, pp. 323-329, 2003.
E. Baharav et al., "The effect of adenosine and the $A_3$ adenosine receptor agonist IB-MECA on joint inflammation and autoimmune diseases models", *Inter. J. Mol. Med.*, vol. 10 (supplement 1), p. S104, abstract 499, 2002.
M. Montesinos et al., "Adenosine $A_{2A}$ or $A_3$ receptors are required for inhibition of inflammation by methotrexate and its analog MX-68", *Arthritis & Rheumatism*, vol. 48, pp. 240-247, 2003.

(Continued)

*Primary Examiner* — Jon P Weber
*Assistant Examiner* — Satyendra Singh
(74) *Attorney, Agent, or Firm* — Browdy and Neimark, PPLC (57) ABSTRACT

Inflammatory state in a subject is assayed by determining the level of expression of $A_3$ adenosine receptor ($A_3AR$) in white blood cells (WBC), e.g. circulating WBCs, from the subject. A high level of expression of $A_3AR$ is indicative of an inflammatory state in the subject. This assay can be used for determining the severity of inflammation in a subject and monitoring the efficacy of anti-inflammatory treatment. Also, the level of expression may be used for selecting patients to receive an anti-inflammatory treatment that comprises an $A_3AR$ agonist.

11 Claims, 9 Drawing Sheets

(56) References Cited

OTHER PUBLICATIONS

L. Madi et al., "The A3 Adenosine Receptor is Highly Expressed in Tumor vs. Normal Cells: Potential Target for Tumor Growth Inhibition", *Clinical Cancer Research*, vol. 10, pp. 4472-4479, 2004.

S. Gessi et al,. "Elevated expression of $A_3$ adenosine receptors in human colorectal cancer is reflected in peripheral blood cells", *Clinical Cancer Research*, vol. 10, pp. 5895-5901, 2004.

Nickoloff, B.J. & Nestle F.O., "Recent insights into the immunopathogenesis of Psoriasis provide new therapeutic opportunities," The Journal of Clinical Investigation, Jun. 2004, 113(12): 1664-1675.

Nikoloff, B.J., et al., "The cytokine and chemokine network in psoriasis," Clinics in Dermatology, 2007, 25"568-573.

Gillissen, A., "Managing asthma in the real world," Int. J. Clin. Pract., Jun. 2004, 58(6): 592-603.

Donahue, K.E. et al., "Systematic review: comparative effectiveness and harms of disease-modifying medications for rheumatoid arthritis," Annals of Internal Medicine, Jan. 2008. 148(2): 124-134.

Gao Z-G & Jacobson, K.A., "A review—emerging adenosine receptor agonists," Expert Opinion Emerging Drugs, 2007 12(3): 478-492.

Rhodes, J.M., & Campbell, B.J., "Inflammation and colorectal cancer: IBD-associated and sporadic cancer compared," TRENDS in Molecular Medicine, Jan. 2002, vol. 8, No. 1, pp. 10-16.

Fishman, P. & Bar-Yehuda, S., "Pharmacology and therapeutic applications of A3 receptor subtype," Current Topics in Medicinal Chemistry, 2003, vol. 3, No. 4, pp. 463-369.

Jeurissen et al. (Arthritis and rheumatism, Aug. 1991) vol. 34, No. B, pp. 961-972) (Abstract).

FIG.5A — Paw
FIG.5B — Synovia
FIG.5C — PB MNC

Inflamed Tissues

Peripheral Hematopoietic Tissue

BIOLOGICAL MARKER FOR INFLAMMATION

FIELD OF THE INVENTION

This invention is in the fields of diagnosis and determining effectiveness of treatment of inflammation and in particular to use therefore of biological markers associated with inflammatory states.

PRIOR ART

The following is a list of prior art which is considered to be pertinent for describing the state of the art in the field of the invention. Acknowledgement of these references herein will at times be made by indicating their number within brackets from the list below.
1. Fishman P, Madi L, Bar-Yehuda S, Barer F, Del Valle L, Khalili K. Evidence for involvement of Wnt signaling pathway in IB-MECA mediated suppression of melanoma cells. *Oncogene.*, 21:4060-4064 (2002).
2. Fishman P, Bar-Yehuda S, Rath-Wolfson L, Ardon E, Barrer F, Ochaion A, Madi L. Targeting the A3 adenosine receptor for cancer therapy: inhibition of Prostate carcinoma cell growth by $A_3AR$ agonist. *Anticancer Res.*, 23:2077-2083 (2003).
3. Madi L, Bar-Yehuda S, Barer F, Ardon E, Ochaion A, Fishman P. A3 adenosine receptor activation in melanoma cells: association between receptor fate and tumor growth inhibition. *J. Bio. Chem.*, 278:42121-42130 (2003).
4. Ohana G, Bar-Yehuda S, Arich A, Madi L, Dreznick Z, Silberman D, Slosman G, Volfsson-Rath L, Fishman P. Inhibition of primary colon carcinoma growth and liver metastasis by the A3 adenosine receptor agonist IB-MECA. *British J. Cancer.*, 89:1552-1558 (2003).
5. Fishman P, Bar-Yehuda S, Ohana G, Ochaion A, Engelberg A, Barer F, Madi L. An agonist to the A3 adenosine receptor inhibits colon carcinoma growth in mice via modulation of GSK-3β and NF-κB. *Oncogene*, 23:2465-2471 (2004).
6. US Patent Application No. 2004016709 A1.
7. Szabo, C., et al. Suppression of macrophage inflammatory protein (MIP)-1α production and collagen-induced arthritis by adenosine receptor agonists. *British J. Pharmacology*, 125:379-387 (1998).
8. Mabley, J., et al. The adenosine $A_3$ receptor agonist, $N^6$-(3-iodobenzyl)-adenosine-5'-N-methyluronamide, is protective in two murine models of colitis. *Europ. J. Pharmacology*, 466:323-329 (2003).
9. Baharav, E., et al. The effect of adenosine and the $A_3$ adenosine receptor agonist IB-MECA on joint inflammation and autoimmune diseases models. *Inter J. Mol. Med.* 10 (supplement 1) page S104, abstract 499 (2002).
10. PCT Application, publication No. WO2005/0063246, entitled "Method for Treatment of Multiple Sclerosis".
11. Montesinos, M. Carmen, et al. Adenosine $A_{2A}$ or $A_3$ receptors are required for inhibition of inflammation by methotrexate and its analog MX-68. *Arthritis & Rheumatism*, 48:240-247 (2003).
12. Madi L, Ochaion A, Rath-Wolfson L, Bar-Yehuda S, Erlanger A, Ohana G, Harish A, Merimski 0, Barer F, Fishman P. The A3 Adenosine Receptor is Highly Expressed in Tumor vs. Normal Cells: Potential Target for Tumor Growth Inhibition. *Clinical Cancer Research*, 10: 4472-4479, 2004.
13. US Patent Application, publication No. 20040137477 A1, entitled "A3AR as a marker for a diseased state".
14. Gessi, S. et al. Elevated expression of $A_3$ adenosine receptors in human colorectal cancer is reflected in peripheral blood cells *Clinical Cancer Research* 10:5895-5901, 2004

BACKGROUND OF THE INVENTION

The $A_3$ adenosine receptor, a $G_i$ protein-associated cell surface receptor, was proposed as a target to combat cancer and inflammation. The receptor is highly expressed in various tumor cell types while expression in adjacent normal tissues is relatively low. Activation of the receptor by a specific synthetic agonist induces modulation of downstream signal transduction pathways which include the Wnt and the NF-kB, resulting in tumor growth inhibition (1-5).

In vivo studies have shown that $A_3AR$ agonists inhibit the development of colon, prostate and pancreatic carcinomas as well as melanoma and hepatoma. $A_3AR$ agonists were also been shown to act as anti-inflammatory agents by ameliorating the inflammatory process in different experimental autoimmune models such as rheumatoid arthritis, Crohn's disease and multiple sclerosis (6-10). It was proposed also that the $A_{2A}$ and $A_3$ receptors mediate the anti-inflammatory effects of methotrexate (11).

$A_3$ adenosine receptor ($A_3AR$) expression levels are elevated in cancer cells as compared to normal cells (12). Thus, the $A_3AR$ expression level has been described as a means for the diagnosis of cancer (13). In addition, $A_3AR$ expression levels have also been described to be elevated in peripheral blood cells of patients with colorectal cancer (14).

GENERAL DESCRIPTION OF THE INVENTION

It is an object of the invention to provide a method for determining an inflammatory state in a subject.

Another object of the invention to provide a method for determining the severity of an inflammatory state in a subject.

It is a further object of the invention to provide a method for determining the effectiveness of an anti-inflammatory therapeutic treatment of a subject.

It is yet a further object of the invention to provide a method for selecting subjects to receive anti-inflammatory therapeutic treatment.

The present invention is based on the surprising finding that there is an increase in the level of $A_3$ adenosine receptor expression in the WBC of a subject who has an inflammatory condition as compared to the WBC of a healthy subject. Furthermore, it was found that in subjects who respond to anti-inflammatory drug treatment, there is a reduction in the level of $A_3$ adenosine receptor expression in their WBC. This finding paves the way for the use of the $A_3$ adenosine receptor expression level as a means for the diagnosis of an inflammatory state, as well as other applications described below.

In a first aspect of the invention, there is provided a method of determining an inflammatory state in a subject that comprises determining the level of expression of $A_3$ adenosine receptor ($A_3AR$) in white blood cells (WBC), e.g. circulating WBCs, from the subject. A high level of expression of $A_3AR$ is indicative of an inflammatory state in the subject.

The sample comprising WBC may be whole blood or may be a blood fraction that contains WBC. At times, it may be desired to use a fraction that includes a specific population of WBC such as mononuclear cells (MNC), sub-populations of MNC—monocytes or lymphocytes, or a sub-population of lymphocytes, e.g. T-cells, B-cell or their sub-populations. A WBC-comprising sample may also at times be obtained from the lymphatic system, e.g. from lymph nodes.

Determining the level of expression may be carried out through determination of the level of $A_3AR$ mRNA as well or the level of $A_3AR$ protein. The term "level of expression" as used herein thus includes the level of $A_3AR$ mRNA as well as the level of $A_3AR$ protein or $A_3AR$ protein fragments in the sampled cells.

It was found that medication may influence the level of the $A_3AR$ expression. Thus, past disease history including prior or current treatment, may influence the $A_3AR$ expression level and my need to be taken into account in the performance of the methods of the invention.

In a second aspect of the invention, there is provided a method for determining the severity of an inflammatory state in a subject comprising determining the level of expression of $A_3AR$ in WBC of the subject; and comparing the level of expression of $A_3AR$ in the cells with the level of prior determined standards that correlate $A_3AR$ expression level with severity of infection. The prior determined standards may include, for example, a set of values, which may be a list of discrete values or a continuous curve, correlating results to a measure of severity of inflammation; or it may be a set of descriptors, such as a qualitative list of possible results and their meanings in respect of severity of inflammation, e.g. if the outcome is manifested as a color reaction, the descriptors may list the range of possible color or color intensity outcomes and their meaning in respect of severity of inflammation; or it may included graphical or pictorial representations of expected assay outcomes for different seventies of inflammation or different inflammatory states; or a set of reference standards, which may be run in parallel with the sample for calibration and evaluation of the data. The standards may typically be obtained by assaying expression level of $A_3AR$ in a plurality of samples from each of a number of inflammatory diseases states to obtain a statistical measure on the correlation between expression level and the disease state. The classification into disease states may for example be binary: light inflammation and severe inflammation. The classification may also include a plurality of different states, such as, for example, light, moderate and severe inflammation. The classification may also be by the use of a numerical value, according to the level of expression, e.g. a number between 1 and 10, for corresponding light through severe inflammation, etc. As will be appreciated, there may be many types of classifications and the invention is not limited to specific types of classifications.

In a third aspect of the invention, there is provided a method for determining the effectiveness of an anti-inflammatory therapeutic treatment of a subject, the treatment comprising administering an $A_3AR$ agonist to the subject. The treatment may be a monotherapy with an $A_3AR$ or a combination therapy of an $A_3AR$ with another drug, such as a combination of an $A_3AR$ with methotrexate. The method comprises determining the expression level of $A_3AR$ in WBCs from the subject in two or more successive time points, at least one of which is during an anti-inflammatory treatment, wherein a difference in the level being indicative of effectiveness of the drug treatment. The successive time points may, for example be one or more taken before an anti-inflammatory treatment and one or more during the treatment, one or more taken during the treatment and one or more taken during a treatment cessation.

The $A_3AR$ level of expression in WBC in accordance with some embodiments of the invention may be used for determining the state or severity of inflammation, e.g. for determining the presence or absence of an inflammatory state. In accordance with other embodiments of the invention, the A3AR level of expression may be used for quantitative determination of the degree of severity of the inflammatory state. Thus, the term "determining" or "determination" as used herein encompasses both quantitative and qualitative determination.

An "inflammatory state" includes any state of active or sub-clinical inflammation. By a preferred embodiment the invention is used for determining an inflammatory state in subjects suffering from and autoimmune inflammatory disease. The inflammation may be due to an inflammatory disease, or it may be a side effect of some other type of disease or disorder. Examples of inflammatory diseases include but are not limited to inflammatory bowel diseases, inflammatory corpuscle, inflammatory fibrous hyperplasia, inflammatory gallbladder disease, inflammatory papillary hyperplasia and autoimmune diseases. Autoimmune diseases may include any of the following: rheumatoid arthritis, Myasthenia Gravis (MG), Congenital myasthenia gravis, Multiple sclerosis (MS), Stiff-man syndrome, Tropical spastic paraparesis, Rasmussen's encephalitis, Acute motor axonal neuropathy, Acute sensory-motor axonal neuropathy, Dorsal root ganglion neuritis, Acute pan-autonomic neuropathy, Brachial neuritis, Acute necrotizing hemorrhagic lekoencephalitis, Sporadic necrotizing myelopathy, Paraneoplastic cerebellar degeneration, Guillain-Barre syndrome, Limbic encephalitis, Opsoclonus-myoclonus ataxia, Sensory neuronitis, Autonomic neuropathy, Demyelinating neuropathy, AIDS-dementia complex, Tourette's syndrome, Miller-Fisher syndrome, Alzheimer's disease, Graves' Disease, Hashimoto's thyroiditis, Postpartum thyroiditis, Focal thyroiditis, Juvenile thyroiditis, Idiopathic hypothyroidism, Type I (insulin dependent) diabetes mellitus, Addison's disease, Hypophysitis, Autoimmune diabetes insipidus, Hypoparathyroidism, Pemphigus Vulgaris, Pemphigus Foliaceus, Bullous phemphigoid, Pemphigoid gestationis, Cicatrical pemphigoid, Dermatitis herpetiformis, Epidermal bullosa acquisita, Erythema multiforme, Herpes gestatonis, Vitiligo, Chronic urticaria, Discoid lupus, Alopecia universalis/Areata, Psoriasis, Autoimmune hepatitis, Primary biliary cirrhosis, Chronic active hepatitis, Chronic active hepatitits/Primary biliary cirrhosis overlap syndrome, Primary sclerosing cholangitis, Autoimmune hemolytic anemia, Idiopathic thrombocytopenic purpura, Evans syndrome, Heparin-induced thrombocytopenia, Primary autoimmune neutropenia, Autoimmune (primary) neutropenia of infancy, Autoimmune neutropenia following bone marrow transplant, Acquired autoimmune hemophilia, Autoimmune gastritis and pernicious anemia, Coeliac disease, Crohn's disease, Ulcerative colitis, Sialadenitis, Autoimmune premature ovarian failure, Azoospermia, Hypogonadism, Male infertility associated with sperm autoantibodies, Autoimmune orchitis, Premature ovarian failure, Autoimmune oophoritis, Uveitis, Retinitis, Sympathetic ophthalmia, Birdshot retinochoroidopathy, Vogt-Koyanagi-Harada granulomatous uveitis, Retinal degeneration, Lens-induced uveitis, Optic neuritis, Autoimmune sensorineural hearing loss, Meniere's disease, Autoimmune myocarditis, Congenital heart block (neonatal lupus), Chagas' disease, Adriamycin cardiotoxicity, Dressler's myocarditis syndrome, Bronchial asthma, Interstitial fibrosing lung disease, Rapidly progressive glomerulonephritis, Autoimmune tubulointerstitial nephritis, Systemic lupus erythematosus (SLE), Antiphospholipid syndrome, Rheumatoid arthritis, Juvenile Rheumatoid arthritis, Felty's syndrome, Large granular lymphocytosis (LGL), Sjogren's syndrome, Systemic sclerosis (scleroderma), Crest syndrome, Mixed connective tissue disease, Polymyositis/dermatomyositis, Goodpasture's Disease, Wegener's granulomatosis, Churg-Strauss syndrome, Henoch-Schonlein purpura, Microscopic polyangiatis, Periarteritis nodosa, Bechet's syndrome, Atherosclerosis, Temporal (giant) cell arteritis, Takayasu arteritis, Kawasaki disease, Ankylosing spondilitis, Reiter's disease, Sneddons disease, Autoimmune polyendocrinopathy, candidiasis-ectodermal dystropy, Essential cryoglobulinemic vasculitis, Cutaneous leukocytoclastic angiitis, Lyme disease, Rheumatic fever and heart disease, Eosinophilic fasciitis, Paroxysmal cold hemoglobinuria, Polymyalgia rheumatica, Fibromyalgia, POEMS syndrome (polyneuropathy, organomegaly, endocrinopathy, M-spot and skin changes), Relapsing polychondritis, Autoimmune lymphoproliferative syndrome, TINU syndrome (acute tubulointerstitial nephritis and uveitis), Common variable immunodeficiency, TAP (transporter associated with antigen presentation) deficiency, Omenn syndrome, HyperlgM syndrome, BTK agammaglobulinemia, Human immunodeficiency virus and Post bone-marrow-transplant.

The sample comprising WBC used in the methods of the invention may include any of the known types of cells which make up this group. In particular, the sample should preferably include mononuclear cells (monocytes and/or lymphocytes). At times, the sample may include in addition, or in the alternative, granulocytes (neutrophils, eosinophils or basophils).

In a first embodiment, a high level of expression of $A_3AR$ is employed as an indicator of an inflammatory state in the subject. The term "high level" is to be understood as meaning a significantly higher level of expression than in normal cells. For example, the level of the $A_3AR$ expression in the WBC may be compared to a control level, the control level being the level of $A_3AR$ expression in normal WBC of a healthy subject. At times it may be useful to determine the expression level by testing an assayed sample from an individual in parallel to one or more reference standards, e.g. one reference standard indicative of a normal state and another indicative of an inflammatory state; or one reference standard indicative of a normal state and two or more of different disease states.

In a second embodiment, the determined expression level is compared to standards. The standards may be based on previously determined levels from healthy individuals and from individuals with an inflammatory state or with different inflammatory states. The standards may be provided, for example, in the form of discrete numeric values or, in case the assay method is colorimetric, in the form of a chart with different colors or shadings for healthy and inflammatory states; or they may be provided in the form of a comparative curve prepared on the basis of such standards.

Such standards may be prepared by determining the level of $A_3AR$ expression (which may be the level of $A_3AR$ protein, protein fragment, or mRNA level etc., as discussed above) present in WBC cells obtained from a plurality of patients positively diagnosed (by other means, for example by a physician, by histological techniques etc.) as having inflammation at varying levels of severity. The severity of the disease for the preparation of the standards may also be determined by various conventional methods such as by pathological techniques. In another embodiment, the assay is carried out in parallel to a number of standards of healthy subjects and subjects of different inflammatory states and the level determined in the assayed sample is then compared to such standards.

For example, a protein content level of between $X_1$ to $X_2$ per 1,000,000 cells may be defined as being indicative of grade 1 inflammation, a higher protein content of $Y_1$ to $Y_2$ per 1,000,000 cells may be defined as being indicative of grade 2 inflammation, etc. After such standards are prepared, it is possible to compare the level of A3AR expression obtained from a specific individual to the corresponding value of the standards, and thus obtain an assessment of the severity of the disease.

The effectiveness of an anti-inflammatory therapeutic treatment of a subject may be assessed by taking samples of WBC at various time points before, during and after the treatment. For example, a first sample may be taken at a time point prior to initiation of the treatment and a second sample may be taken at a time point during the treatment. A decrease in the level of the $A_3AR$ expression in the second sample as compared to the first sample would be indicative that the treatment is effective. The degree of decrease could be indicative of the degree of effectiveness of the treatment, i.e. the correlation would be quantitative.

In another example, a first sample may be taken at a time point during the treatment and a second sample may be taken at a time point during the treatment subsequent to the time point of the first sample. A decrease in the level of the $A_3AR$ expression in the second sample as compared to the first sample would be indicative that the treatment is effective.

In a third example, a first sample may be taken at a time point during the treatment and a second sample may be taken at a time point after the treatment has been discontinued. In this case, an increase in the level of the $A_3AR$ expression in the second sample as compared to the first sample would be indicative that the treatment is effective.

Of course, various other combinations may be carried out, as well as the taking of samples at more than two time points.

The invention also provided a method for selecting a subject suffering from a certain inflammatory disease, to receive anti-inflammatory therapeutic treatment that comprises administering to the subject an $A_3$ adenosine receptor ($A_3AR$) agonist, the method comprising determining the level of expression of $A_3AR$ in the WBCs of the subject and selecting the subject to receive said anti-inflammatory therapeutic treatment if said level is above a predetermined level. Said predetermined level may be a certain threshold level for all subjects. Said predetermined level may also be a range of levels for different patient groups, for example: for different age groups; for different disease states; for different disease histories—histories of past medication (for example, methotrexate was found to induce an increase in the level of $A_3AR$) number of years having the disease, etc. Said predetermined level may be determined through clinical studies that look for correlation between receptor expression and a drug response according to one of the acceptable response criteria, such as the ACR20, ACR50 and ACR70 set by the American College of Rheumatology, or any other acceptable efficacy criteria.

Selection of subjects suitable for anti-inflammatory treatment may be executed by determining the level of expression of $A_3AR$ in a sample of WBC withdrawn from said subject before treatment. The subject is selected if the determined level of $A_3AR$ is above a predefined threshold.

According to one embodiment, the threshold is a certain multiple of the level of $A_3AR$ expression in WBC of a healthy subject. According to another embodiment, the threshold is determined on the basis of the average expression level in patients having said certain inflammatory disease, and may be said average or a certain multiple or fraction thereof. By a further embodiment, the threshold is determined on the basis of clinical studies in human patients that are designed to determine the correlation between the level of expression and the response of the patients to said therapeutic treatment. As will be appreciated, the threshold may be different for different inflammatory diseases. As may also be appreciated, by its nature such a selection criterion is based on statistics and thus signifies a certain probability that a selected patient may respond to a treatment. Thus, such a selection criterion, as will no doubt be appreciated by a person versed in the art, such selction criteria may not be completely predictive as to response and there may also be a certain fraction of patients selected in this was who will not respond to the treatment.

The selection method may also apply for selecting candidates for participating in clinical studies to test the efficacy of anti-inflammatory treatments comprising administering to patients an $A_3AR$ agonist, either alone or in combination with other drugs such as methotrexate. As appreciated by those versed in the art, a clinical study (also known by the terms 'clinical trial' or 'clinical protocol'), is a scientific study in human volunteers to determine how a new medicine or treatment works in human subjects. Interventional trials determine whether experimental treatments or new ways of using known therapies are safe and effective under controlled environments. It is through clinical studies that physicians find new and better ways to prevent, detect, diagnose, control, and treat illnesses. The clinical studies for which patients are selected, in accordance with the invention, based on the $A_3AR$ level may be Phase I, Phase II, Phase III, Phase IV or any other type of clinical study.

BRIEF DESCRIPTION OF THE FIGURES

In order to understand the invention and to see how it may be carried out in practice, a preferred embodiment will now be described, by way of non-limiting example only, with reference to the accompanying drawings, in which.

EXAMPLES

Materials and Methods

Induction of Adjuvant Induced Arthritis (AIA) Model in Rats

Female Lewis rats, aged 8-12 weeks were obtained from Harlan Laboratories (Jerusalem, Israel). Rats were maintained on a standardized pelleted diet and supplied with tap water. Experiments were performed in accordance with the guidelines established by the Institutional Animal Care and Use Committee at Can-Fite BioPharma, Petah Tikva, Israel. The rats were injected subcutaneously (SC) at the tail base with 100 μl of suspension composed of incomplete Freund's adjuvant (IFA) with 10 mg/ml heat killed Mycobacterium tuberculosis, (Mt) H37Ra, (Difco, Detroit, USA). Each group contained 10 animals.

Treatment with IB-MECA (10 μg/kg) was initiated on day 14 after vaccination and was orally administered by gavage, twice daily. Another group was treated with Methotrexate (MTX) (1.5 mg/kg) intraperitoneally every 3 days, starting on day 14th after vaccination. The control group in each experiment received vehicle only (DMSO in a dilution corresponding to that of the drugs).

Clinical Disease Activity Score was assessed as follows: the animals were inspected every second day for clinical arthritis. The scoring system ranged from 0-4 of each limb: 0—no arthritis; 1—redness or swelling of one toe/finger joint; 2—redness and swelling of more than one toe/finger joints, 3—the ankle and tarsal-metatarsal joints involvement. 4—entire paw redness or swelling The clinical score was calculated by adding the four individual legs' score. The inflammatory intensity was also determined in accordance with the increase in the rat hind paw's diameter, measured by caliper (Mitotoyo, Tokyo, Japan).

Separation of Inflammatory and Hematopoietic Tissues and Preparation of Protein Extracts a. Inflammatory Tissues The hind paws were dissected above the ankle joint. The bony tissue was broken into pieces, snap frozen in liquid nitrogen and stored at −80° C. until use. To prepare a protein extract, RIPA buffer (containing 150 mM NaCl, 50 mM Tris, 1% NP40, 0.5% Deoxycholate and 0.1% SDS) was added to the paw tissue (4 ml/gr of tissue). The mixture was homogenized on ice with a polytron and centrifuged.

Synovial tissue was removed and synovial cells were separated by incubating the tissue in RPMI containing 1 mg/ml Collagenase IV and 0.1 mg/ml DNase with a vigorous shaking (200 rpm) at 37° C. for 30 min. The supernatant containing the synovial cells was collected and the undigested tissue was re-extracted. The supernatants from both extractions were combined and cells were washed with PBS. Protein extracts were prepared.

b. Hemopoietic Tissues

Lymph nodes were removed and cells were separated by first mincing the tissue and disaggregating it through a needle of 22 G Spleens were removed and subjected to Lymphoprep (Nycomed AS, Oslo, Norway) for mononuclear cell separation. Protein extracts were prepared.

Separation of Peripheral Blood Mononuclear Cells from RA Patients and Healthy Subjects Blood was withdrawn from healthy subjects or RA patients. Mononuclear cells (lymphocytes and monocytes) were separated using Ficoll-Hypaque gradient. Protein was extracted from the mononuclear cells.

Clinical Study

Blood was withdrawn from RA patients who were enrolled in a clinical study sponsored by Can-Fite BioPharma, in which the effect of CF101, a clinical grade IB-MECA, on arthritic patients was evaluated. The patients randomly received 0.1, 1.0 or 4.0 mg of CF 101 twice daily. Blood was withdrawn at 2 time points: (a) after a washout period of 4-6 weeks from a previous treatment and before CF101 treatment was initiated—this was considered as baseline level; (b) after 3 months of treatment with CF101. Peripheral blood mononuclear cells were separated and protein was extracted as described above. In addition, C reactive protein (CRP) values, the number of tender and swollen joints, the physicians global assessment, the patient own assessment, the pain score and the disability score were recorded and the ACR score was calculated for each patient (ACR is a score that is calculated according to criteria established by the American College of Rheumatology, based on the aforementioned measures, to evaluate the effectiveness of drugs for treatment of RA; ACR 20, ACR 50 and ACR 70 respectively represent a 20%, 50% and 70% improvement in this score).

Analysis of $A_3AR$ Protein Expression Level by Western Blot (WB)

Western blot analysis (WB) of synovial, paw, spleen and lymph nodes were carried out according to the following protocol. Samples were rinsed with ice-cold PBS and transferred to ice-cold lysis buffer (TNN buffer, 50 mM Tris buffer pH=7.5, 150 mM NaCl, NP 40). Cell debris was removed by centrifugation for 10 min, at 7500×g. Protein concentrations were determined using the Bio-Rad protein assay dye reagent. Equal amounts of the sample (50 μg) were separated by SDS-PAGE, using 12% polyacrylamide gels. The resolved proteins were then electro-blotted onto nitrocellulose membranes (Schleicher & Schuell, Keene, N.H., USA). Membranes were blocked with 1% BSA and incubated with the primary antibody against $A_3AR$ (dilution 1:1000) for 24 h at 4° C. Blots were then washed and incubated with a secondary antibody for 1 h at room temperature. Bands were recorded using BCIP/NBT color development kit (Promega, Madison, Wis., USA).

Results $A_3AR$ is Up-Regulated in Inflammatory and Hematopoietic Tissues

Figure 1A:
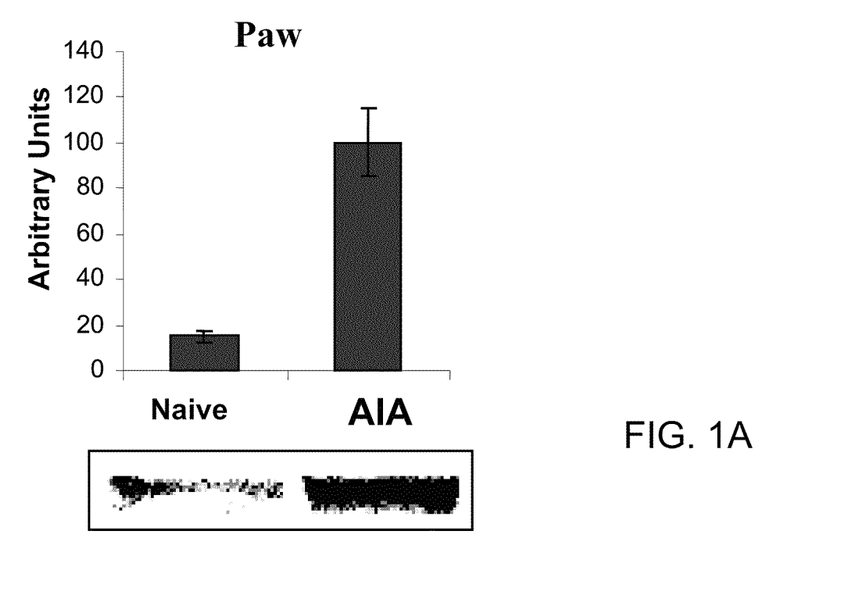
FIGS. 1A-1D depict exemplary Western blots and corresponding bar graphs of average blot intensity and standard error showing that $A_3AR$ is up-regulated in inflammatory and hematopoietic tissues upon occurrence of inflammation.
Figure 1B:
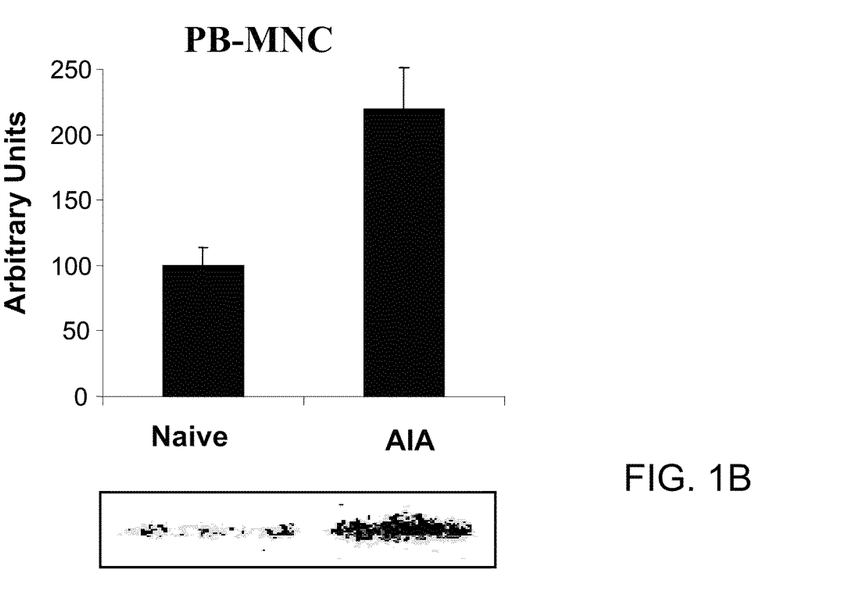
Figure 1C:
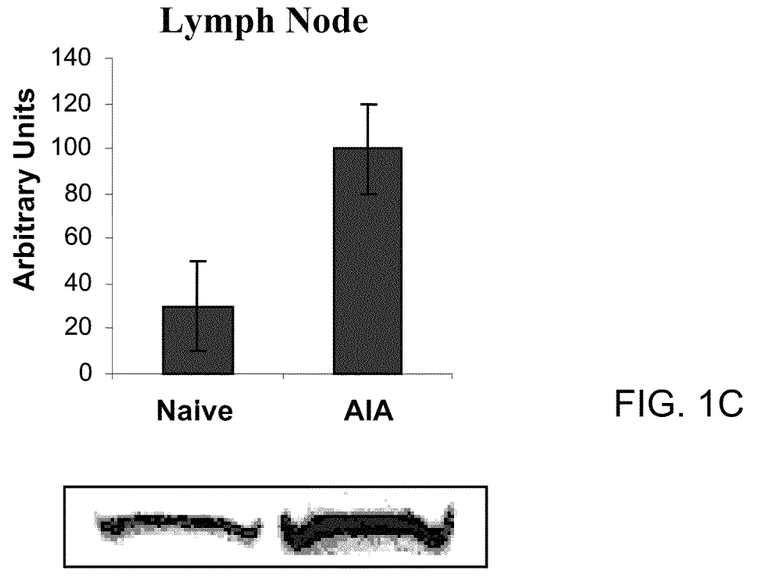
Figure 1D:
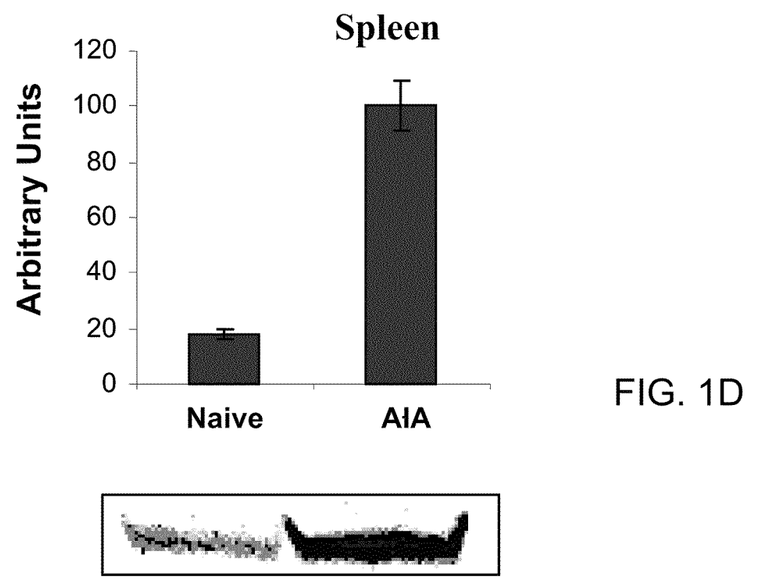

The level of expression of $A_3AR$ in AIA model was determined by WB analysis. To this end, protein extracts from inflamed tissue (paw) or from peripheral hematopoietic tissue (peripheral blood mononuclear cells, lymph nodes and spleen) were obtained and analyzed as described in the Materials and Methods. FIGS. 1A-1D present WB analysis results, also presented in corresponding bar graphs, which give average results and the standard deviation. As shown, $A_3AR$ is up-regulated in inflamed tissue (FIG. 1A) as well as in peripheral hematopoietic tissues (FIGS. 1B-1D).

Figure 2:
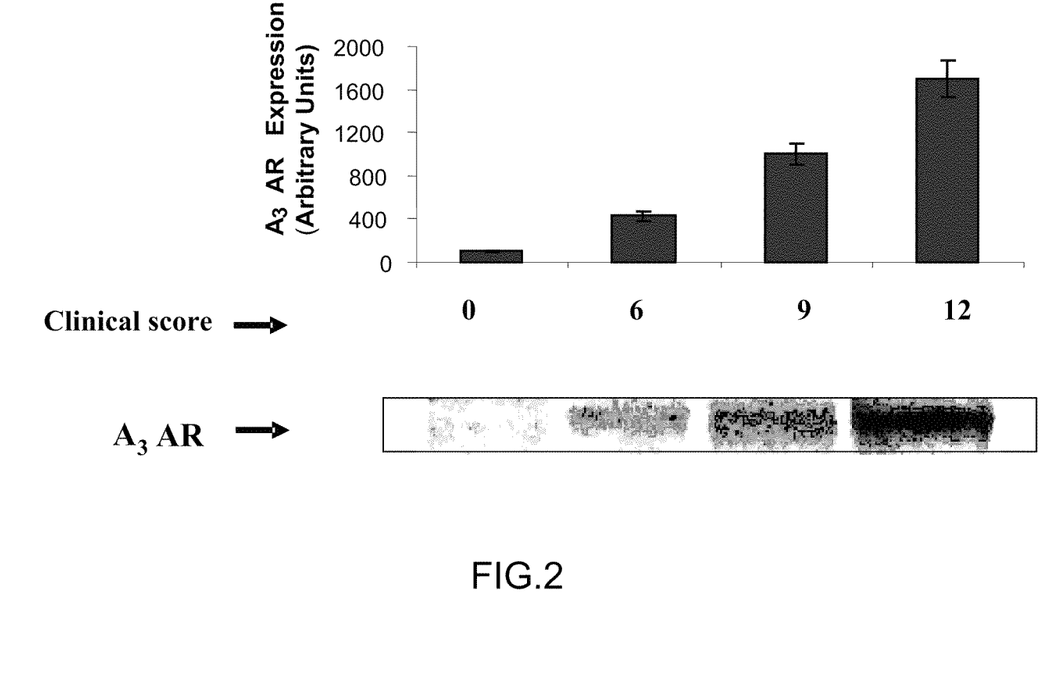
FIG. 2 depicts a Western blot and the corresponding bar graph of average blot intensity and standard error showing that the level of expression of $A_3AR$ correlates with Disease Clinical Score in AIA model. "0" indicates Naïve animals (animals without inflammation) and "6", "9" and "12" relate to inflamed animals and the numbers indicate the inflammatory score in these animals.

The level of expression of $A_3AR$ in AIA model correlated also with Disease Clinical Score (FIG. 2) providing further evidence for the correlation between inflammation and $A_3AR$ expression.

CF101 Inhibits the Development of AIA

Figure 3:
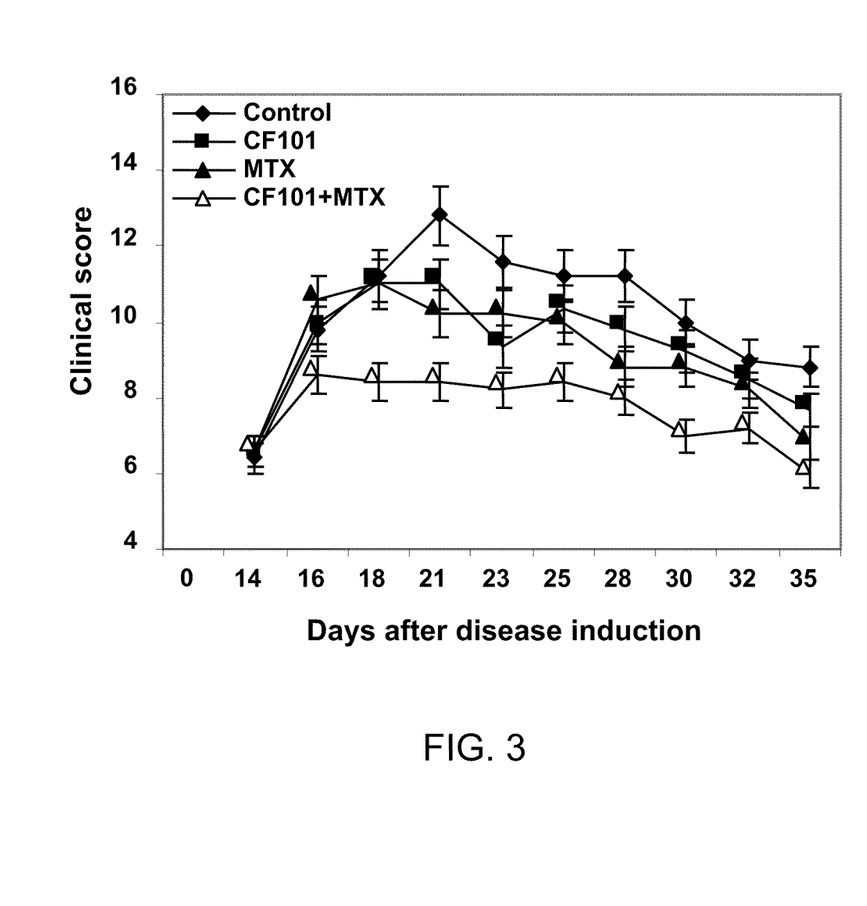
FIG. 3 is a graph showing the change in severity of arthritis as a function of time in control animals and in AIA animals treated with either methotrexate (MTX), CF101 (clinical grade IB-MECA), a combination of MTX and CF101 or vehicle only (control).

About 21 days after immunization, most of the vehicle treated animals progressively developed arthritis. CF101 treatment (10 μg/kg, given orally twice daily, starting on day 14th after immunization) and methotrexate (MTX) treatment resulted in a significant decrease in disease severity, very similar for both drugs, as was evaluated by the arthritis clinical score. Disease peaked on days 21-28 and maximal effect of CF101 or MTX was seen on these days (FIG. 3).

Figure 4A:
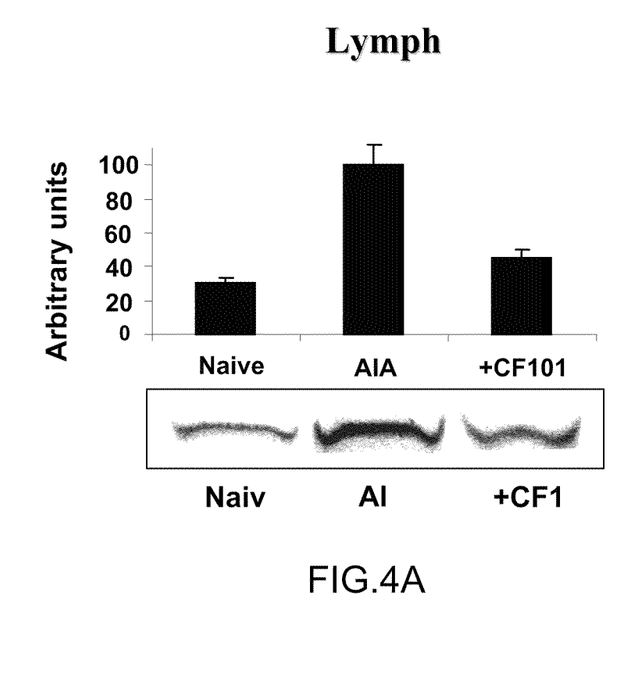
FIGS. 4A-4B depict exemplary Western blots and corresponding bar graphs with standard errors showing $A_3AR$ protein expression level in lymph node (FIG. 4A) and spleen (FIG. 4B) cells in naïve animals, in AIA animal and in AIA animals after CF 101 (clinical grade IB-MECA) treatment.
Figure 4B:
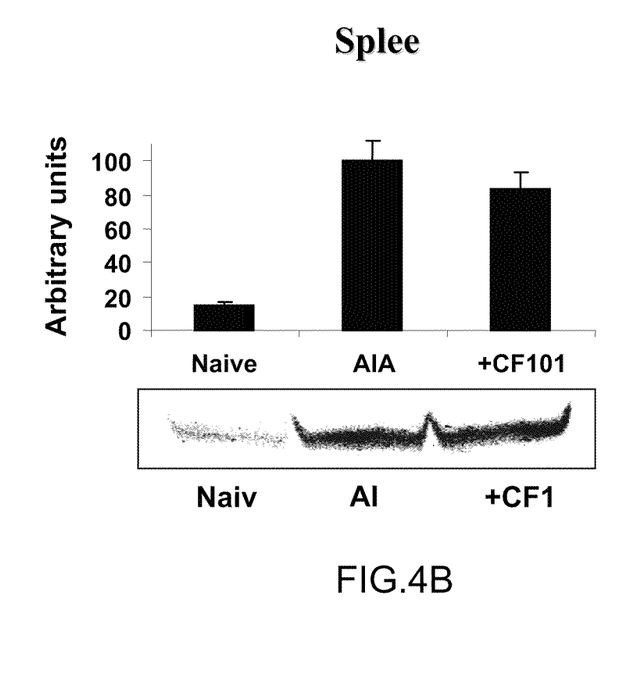
Figure 5A:
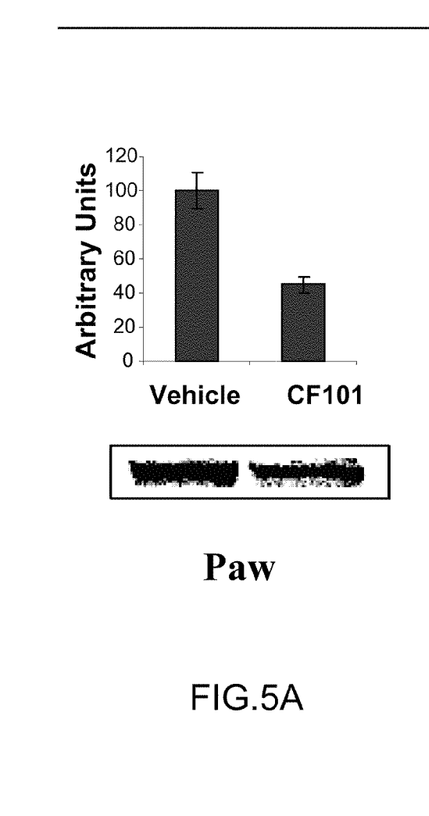
FIGS. 5A-5C depict an exemplary Western blots and the corresponding bar graphs with standard errors showing $A_3AR$ protein expression level in paw (FIG. 5A), synovial tissue (FIG. 5B) and peripheral blood mononuclear cell (FIG. 5C) in AIA either vehicle treated or treated with CF101.
Figure 5B:
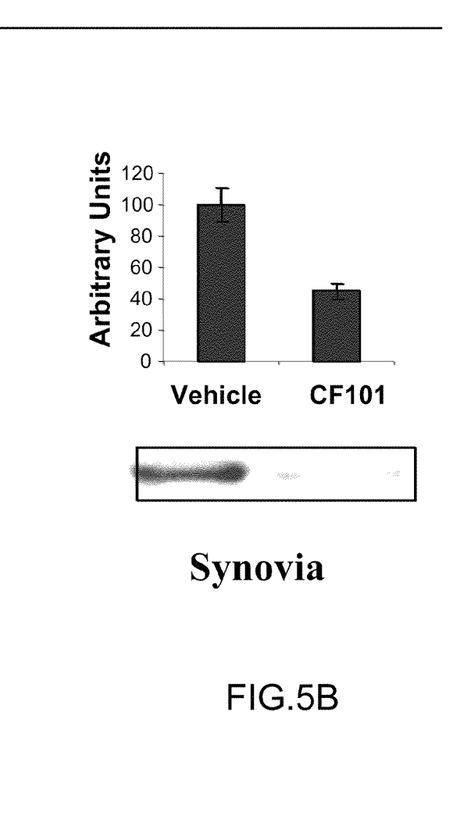
Figure 5C:
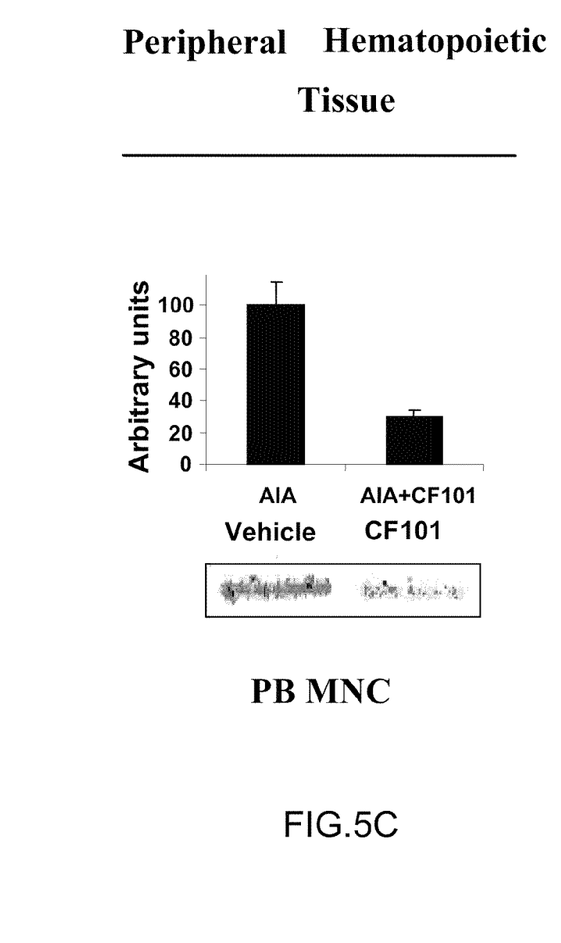
Figure 6:
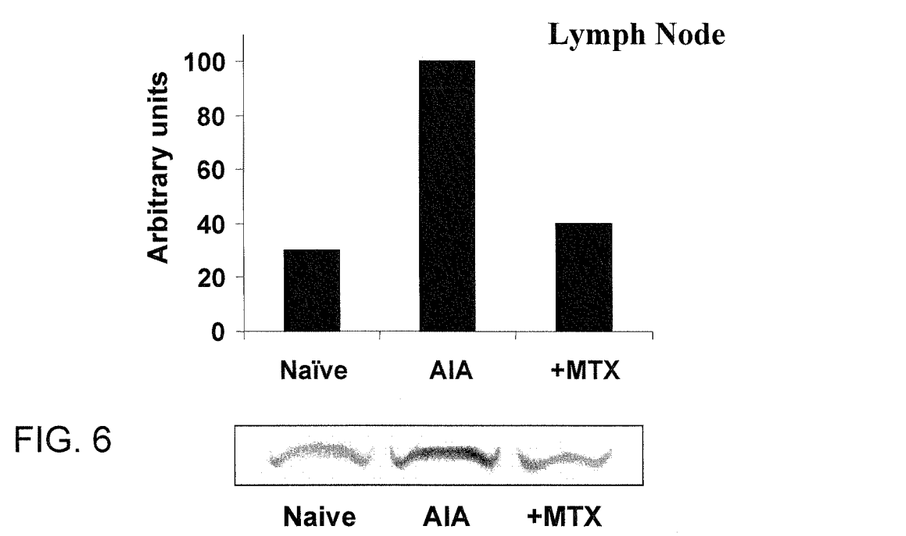
FIG. 6 depicts a Western blot and the corresponding bar graph showing $A_3AR$ protein expression level in lymph nodes in naïve animals, MA animals and in AIA animals treated with MTX.

$A_3AR$ is Highly Expressed in Inflammatory Tissues and in Peripheral Hematopoietic Tissues of AIA Rats Low $A_3AR$ expression level was detected in the healthy paw & synovial tissues. In the inflammatory tissues derived from AIA rats, a marked increase in the $A_3AR$ protein expression level was noted (FIGS. 4A-4B). Upon IB-MECA treatment $A_3AR$ level was down-regulated (FIGS. 4A-4B). A similar pattern was noted in the peripheral hematopoietic tissues, i.e., low $A_3AR$ expression level was noted in the spleen and lymph node (LN) derived from naïve animals, high in the tissues from AIA and low expression in the tissues of IB-MECA treated rats (FIGS. 5A-5C). In LN derived from AIA rats treated with MTX, a similar $A_3AR$ expression profile was observed (FIG. 6).

Figure 7:
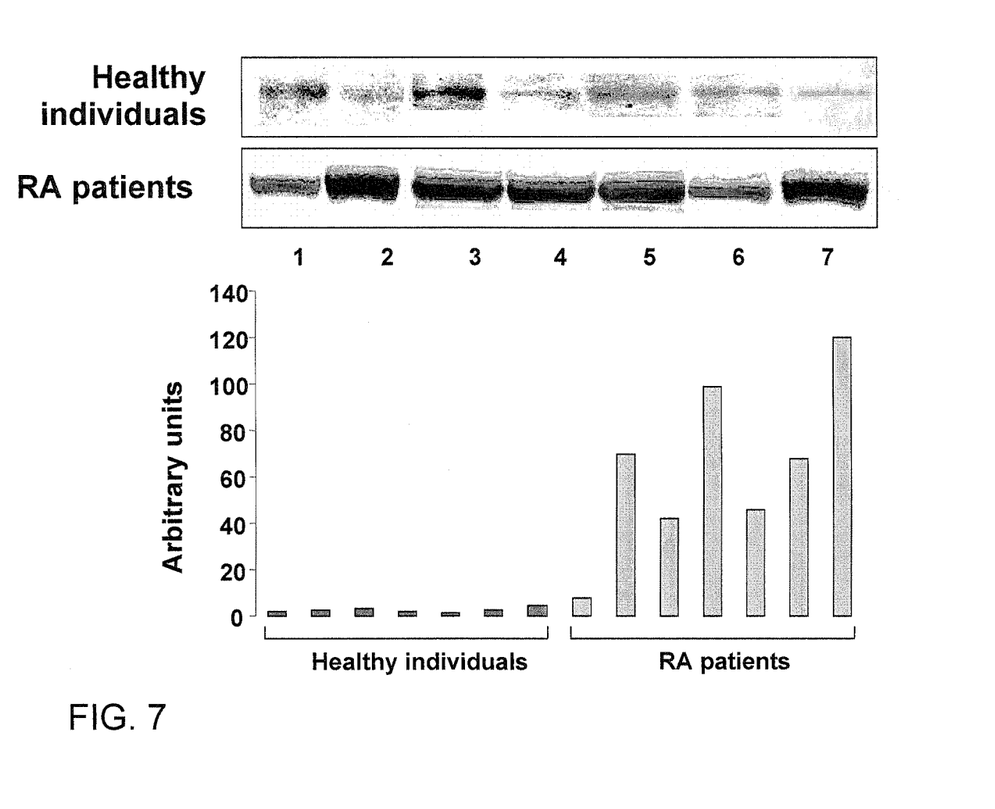
FIG. 7 depicts a Western blot and the corresponding bar graph showing $A_3AR$ protein expression level in 7 healthy subjects and in 7 RA patients.

High $A_3AR$ Expression is Found in MNC Derived from RA vs. Low in Healthy Subjects Low $A_3AR$ expression level was found in MNC from healthy subjects whereas high expression was detected in MNC derived from RA patients (FIG. 7).

Correlation Between $A_3AR$ Expression and Clinical Efficacy Parameters

Figure 8:
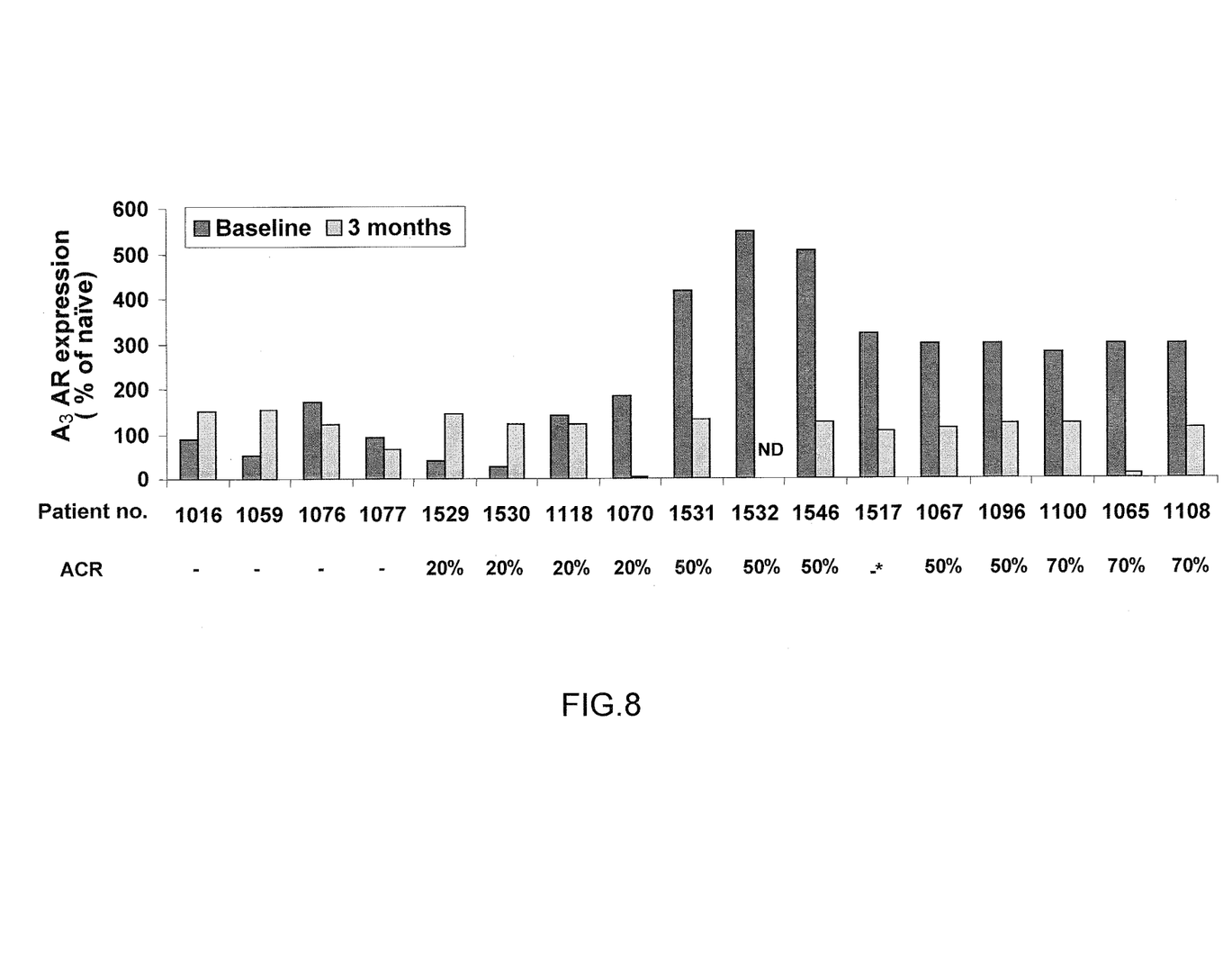
FIG. 8 is a bar graph showing $A_3AR$ level in peripheral blood mononuclear cells of RA patients before and after 3 months of treatment with CF 101. For each patient the response in % according to ACR criteria (criteria for determining efficacy of drugs for treating RA, set down by the American College of Rheumatology).

Blood was withdrawn from 17 RA patients who participated in a clinical study for testing the effect of CF 101 on the manifestation of disease in such patients. The blood was withdrawn following a washout period from previous treatment and then after 3 months of treatment, peripheral blood mononuclear cells (PBMNC) were separated and the level of $A_3AR$ was determined in these cells. As can be seen in FIG. 8, out of these 17 patients, 5 were non-responders, namely these patients have not even achieved an ACR 20 response, while the other 13 patients were responders as they had at least an ACR 20 response (as can be seen in FIG. 8, 3 of the responders had an ACR 70 response, 5 achieved an ACR 50 response and another 4 an ACR 20 only response).

As can further be seen in FIG. 8, all ACR 50 and ACR 70 responders had an initial high level of $A_3AR$, which was reduced after 3 months treatment, while there was essentially no change in the $A_3AR$ level in the non-responders. The patient marked by an "*" (patient no. 1517), while having no ACR response (in view of the fact that the change in the CRP level, one of the parameters used for calculating the ACR score—see below, was below 0%), had a very significant improvement in other parameters, particularly the number of swollen and tender joints.

These data clearly demonstrate the ability to use the $A_3AR$ level in order to predict a response of patient to an anti-inflammatory drug therapy, particularly such therapy which makes use of an $A_3AR$ agonists as a disease modifying drug.

Up Regulation of $A_3AR$ Expression Level in Methotrexate Treated RA Patients

Figure 9:
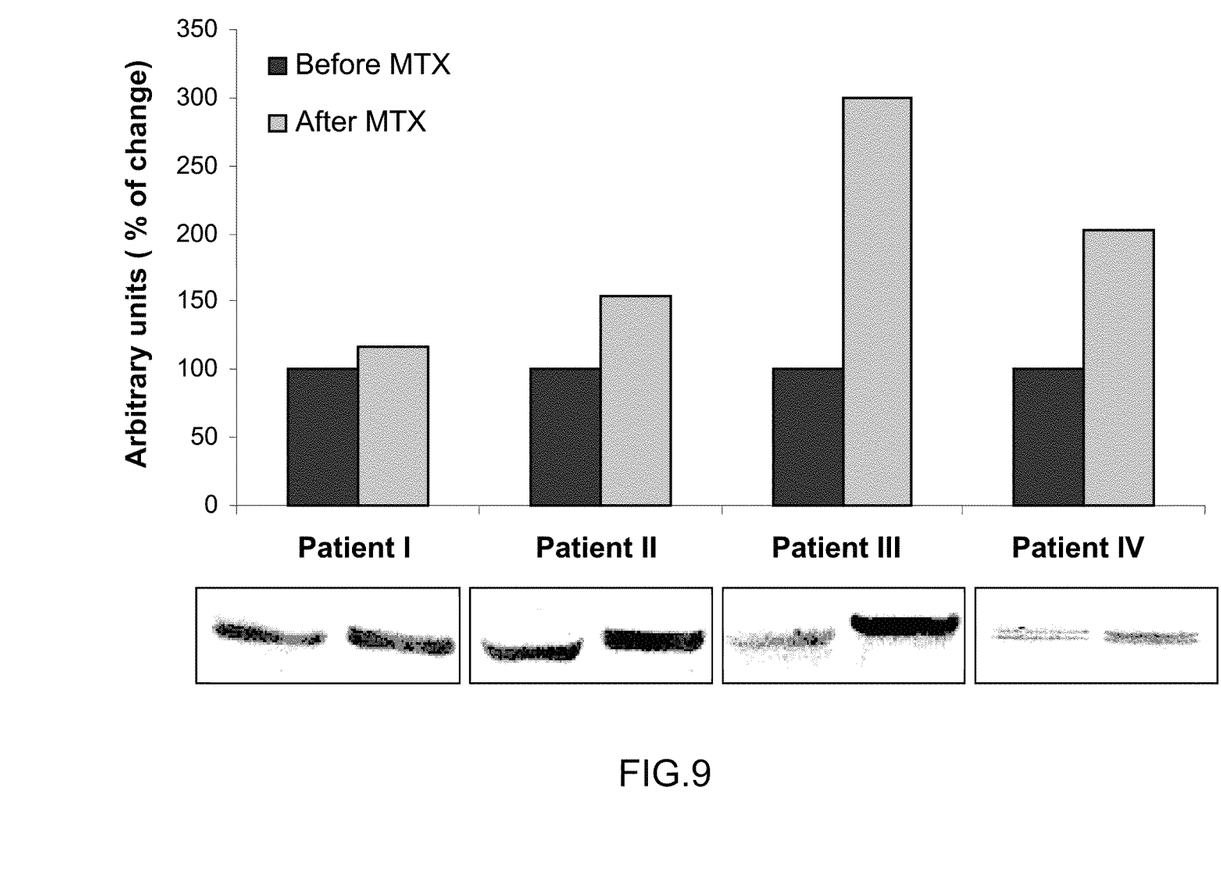
FIG. 9 shows Western blots of $A_3AR$ expression in PBMNCs and corresponding bar graphs of expression intensity in 4 patients before (dark columns) and after (grey columns) and during methotrexate treatment, measured in arbitrary units.

Blood samples were taken from 4 RA patients prior to and after onset of treatment with methotrexate. PBMNCs were separated and the $A_3AR$ levels were assayed as described above. The results that are shown in FIG. 9, demonstrate that treatment with methotrexate induces an increase in the level of the $A_3AR$.

These data show that past disease history, in particular past medication, may influence the $A_3AR$ level in PBMNCs and this history may need to be taken into account for the performance of methods according to the invention.

The invention claimed is:

1. A therapeutic method, comprising:
   a. determining the level of $A_3$ adenosine receptor ($A_3AR$) in a sample of white blood cells (WBCs) of a subject; and
   b. treating the subject only if said level is above a predefined threshold which is about twice the level of $A_3AR$ in WBC of healthy subjects; wherein
      (i) the subject is one that is known to have an inflammatory state,
      (ii) the treating comprises administering an anti-inflammatory agent to the subject, and
      (iii) the anti-inflammatory agent is $N^6$-(3-iodobenzyl)-adenosine-5'-N-methyluronamide (IB-MECA); wherein the treating step comprises treating the subject with an amount of IB-MECA that is effective to reduce the inflammatory state in said subject.

2. The method of claim 1, wherein the sample of WBC is taken from a subject before receiving the anti-inflammatory treatment.

3. The method of claim 1, wherein the autoimmune disease is rheumatoid arthritis (RA).

4. A method for anti-inflammatory therapeutic treatment of a subject known to have an inflammatory state that is the result of an autoimmune disease, the method comprising:
   a. determining the level of $A_3$ adenosine receptor ($A_3AR$) in a sample of white blood cells (WBCs) of the subject; and
   b. treating the subject with an anti-inflammatory agent only if the level is above a predefined threshold which is about twice the level of $A_3AR$ in WBC of healthy subjects; wherein the anti-inflammatory agent is $N^6$-(3-iodobenzyl)-adenosine-5'-N-methyluronamide (IB-MECA) and the amount of the $A_3AR$ agonist is effective to reduce the inflammatory state in said subject.

5. The method of claim 4, wherein the sample of WBC is taken from the subject before receiving the anti-inflammatory treatment.

6. In a method for anti-inflammatory therapeutic treatment of a subject known to have an inflammatory state that is the result of an autoimmune disease, the method comprising treating the subject with an effective amount of $N^6$-(3-iodobenzyl)-adenosine-5'-N-methyluronamide (IB-MECA),
   wherein the improvement comprises selecting the subject to receive the anti-inflammatory therapeutic treatment if determined to have a level of $A_3$ adenosine receptor ($A_3AR$), in a sample of white blood cells (WBCs) of the subject, above a predefined threshold that is about twice the level of $A_3AR$ in WBC of healthy subjects, and withholding said treatment if determined to have a level of $A_3AR$, in a sample of WBCs of the subject, below the predefined threshold.

7. The method of claim 6, wherein the sample of WBCs is taken from a subject before receiving the anti-inflammatory treatment.

8. The method of claim 6, wherein the autoimmune disease is rheumatoid arthritis (RA).

9. A therapeutic method, comprising:
   a. determining the level of $A_3$ adenosine receptor ($A_3AR$) in a sample of white blood cells (WBCs) of a subject; and
   b. treating the subject only if said level is above a predefined threshold which is about twice the level of $A_3AR$ in WBC of healthy subjects; wherein
      (i) the subject is one that is known to have rheumatoid arthritis,
      (ii) the treating comprises administering an anti-inflammatory agent to the subject, and
      (iii) the anti-inflammatory agent is an $A_3AR$ agonist;
   wherein the $A_3AR$ agonist is $N^6$-(3-iodobenzyl)-adenosine-5'-N-methyluronamide (IB-MECA), and the amount of the $A_3AR$ agonist administered is effective to reduce the inflammatory state in said subject.

10. A method for anti-inflammatory therapeutic treatment of a subject known to have rheumatoid arthritis, the method comprising:
    a. determining the level of $A_3$ adenosine receptor ($A_3AR$) in a sample of white blood cells (WBCs) of the subject; and
    b. treating the subject with an anti-inflammatory agent only if the level is above a predefined threshold which is about twice the level of $A_3AR$ in WBC of healthy subjects;
    wherein the anti-inflammatory agent is an $A_3AR$ agonist $N^6$-(3-iodobenzyl)-adenosine-5'-N-methyluronamide (IB-MECA), and the amount of said $A_3AR$ agonist is effective to reduce the inflammatory state in said subject.

11. In a method for anti-inflammatory therapeutic treatment of a subject known to have rheumatoid arthritis, the method comprising treating the subject with an $A_3$ adenosine receptor ($A_3AR$) agonist,
    wherein the improvement comprises selecting the subject to receive the anti-inflammatory therapeutic treatment if determined to have a level of $A_3AR$, in a sample of white blood cells (WBCs) of the subject, above a predefined threshold that is about twice the level of $A_3AR$ in WBC of healthy subjects, and withholding said treatment if determined to have a level of $A_3AR$, in a sample of WBCs of the subject, below said predefined threshold;
    wherein the $A_3AR$ agonist is $N^6$-(3-iodobenzyl)-adenosine-5'-N-methyluronamide (IB-MECA) and the amount of the $A_3AR$ agonist is effective to reduce the inflammatory state in said subject.

* * * * *